(12) United States Patent
Acker et al.

(10) Patent No.: US 6,366,799 B1
(45) Date of Patent: Apr. 2, 2002

(54) MOVABLE TRANSMIT OR RECEIVE COILS FOR LOCATION SYSTEM

(75) Inventors: David E. Acker, Setauket, NY (US); Joel Zilberstein, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 09/117,791

(22) PCT Filed: Feb. 14, 1997

(86) PCT No.: PCT/US97/02440

§ 371 Date: Sep. 25, 1998

§ 102(e) Date: Sep. 25, 1998

(87) PCT Pub. No.: WO97/29683

PCT Pub. Date: Aug. 21, 1997

Related U.S. Application Data
(60) Provisional application No. 60/012,241, filed on Feb. 26, 1996, and provisional application No. 60/011,720, filed on Feb. 15, 1996.

(51) Int. Cl.⁷ .................................................. A61B 5/05
(52) U.S. Cl. ...................................................... 600/424
(58) Field of Search ................................. 600/411, 414, 600/417, 426, 427, 429, 424; 128/899; 606/130

(56) References Cited

U.S. PATENT DOCUMENTS

| | | | |
|---|---|---|---|
| 3,644,825 A | 2/1972 | Davis, Jr. et al. | 324/41 |
| 3,868,565 A | 2/1975 | Kuipers | 324/34 R |
| 4,017,858 A | 4/1977 | Kuipers | 343/100 R |
| 4,054,881 A | 10/1977 | Raab | 343/112 R |
| 4,560,930 A | 12/1985 | Kouno | 324/207 |
| 4,570,354 A | 2/1986 | Hindes | 33/534 |
| 4,592,356 A | 6/1986 | Gutierrez | |
| 4,613,866 A | 9/1986 | Blood | 343/448 |
| 4,642,786 A | 2/1987 | Hansen | 364/559 |
| 4,651,436 A | 3/1987 | Gaal | 33/533 |

(List continued on next page.)

FOREIGN PATENT DOCUMENTS

| | | |
|---|---|---|
| WO | WO 94/00050 | 1/1994 |
| WO | WO 94/04938 | 3/1994 |
| WO | WO 94/06349 | 3/1994 |
| WO | WO 94/23647 | 10/1994 |
| WO | WO 94/28782 | 12/1994 |
| WO | WO 95/05773 | 3/1995 |
| WO | WO 95/07657 | 3/1995 |
| WO | WO 95/09562 | 4/1995 |
| WO | WO 95/10226 | 4/1995 |
| WO | WO 95/19738 | 7/1995 |

(List continued on next page.)

OTHER PUBLICATIONS

"Effects of laser irradiation delivered by flexible fiberoptic system on the left ventricular internal myocardium" American Heart Journal, Sep. 1983, pp. 587–590.

Dorothy Bonn, "High–Power laser help the Ischaemic Heart", The Lancet, vol. 348 (Jul. 13, 1996) p. 118.

Mahmood Mirhoseini et al. "Transmyocardial Laser Revascularization: A Review" Journal of Clinical Laser Medicine & Surgery. vol. 11(1993) pp. 15–19.

*Primary Examiner*—Ruth S. Smith
(74) *Attorney, Agent, or Firm*—Louis J. Capezzuto

(57) ABSTRACT

A system for determining the disposition of a probe within the body of a patient includes a probe having probe field transducers and one or more reference field transducers. The reference field transducers are affixed to a rigid but repositionable frame constructed to allow the transducers to be positioned in close proximity to the body. Non-ionizing fields are transmitted and detected between the probe and reference field transducers, and from the detected fields the relative disposition of the probe with respect to the reference field transducers is determined.

9 Claims, 11 Drawing Sheets

U.S. PATENT DOCUMENTS

| | | | |
|---|---|---|---|
| 4,710,708 A | 12/1987 | Rorden et al. ............... 324/207 |
| 4,788,987 A | 12/1988 | Nickel | |
| 4,849,692 A | 7/1989 | Blood ........................ 324/208 |
| 4,869,238 A | 9/1989 | Opie et al. | |
| 4,905,698 A | 3/1990 | Strohl, Jr. et al. | |
| 4,917,095 A | 4/1990 | Fry et al. | |
| 4,921,482 A | 5/1990 | Hammerslag et al. ......... 604/95 |
| 4,931,059 A | 6/1990 | Markham .................... 606/185 |
| 4,945,305 A | 7/1990 | Blood ................. 324/207.117 |
| 5,002,137 A | 3/1991 | Dickinson et al. ............ 175/19 |
| 5,042,486 A | 8/1991 | Pfeiler et al. | |
| 5,059,197 A | 10/1991 | Urie et al. ................... 604/164 |
| 5,078,144 A | 1/1992 | Sekino et al. | |
| 5,099,845 A | 3/1992 | Besz et al. | |
| 5,125,924 A | 6/1992 | Rudko .......................... 606/12 |
| 5,125,926 A | 6/1992 | Rudko et al. .................. 606/19 |
| 5,158,084 A | 10/1992 | Ghiatas | |
| 5,172,056 A | 12/1992 | Voision ................. 324/207.17 |
| 5,195,540 A | 3/1993 | Shiber ......................... 128/898 |
| 5,195,968 A | 3/1993 | Lundquist et al. ............ 604/95 |
| 5,197,482 A | 3/1993 | Rank et al. | |
| 5,211,165 A | 5/1993 | Dumoulin et al. | |
| 5,215,680 A | 6/1993 | D'Arrigo .................... 252/307 |
| 5,217,484 A | 6/1993 | Marks ........................ 606/200 |
| 5,234,426 A | 8/1993 | Rank et al. ..................... 606/1 |
| 5,251,635 A | 10/1993 | Dumoulin et al. | |
| 5,253,647 A | 10/1993 | Takahashi et al. | |
| 5,255,680 A | 10/1993 | Darrow et al. | |
| 5,265,610 A | 11/1993 | Darrow et al. | |
| 5,267,960 A | 12/1993 | Hayman et al. ............ 604/106 |
| 5,273,025 A | 12/1993 | Sakiyama et al. | |
| 5,275,166 A | 1/1994 | Vaitekunas et al. | |
| 5,295,484 A | 3/1994 | Marcus et al. | |
| 5,295,486 A | 3/1994 | Wollschager et al. | |
| 5,301,682 A | 4/1994 | Debbas | |
| 5,309,913 A | 5/1994 | Kormos et al. | |
| 5,325,873 A | 7/1994 | Hirschi et al. .............. 128/899 |
| 5,368,564 A | 11/1994 | Savage ........................ 604/95 |
| 5,368,592 A | 11/1994 | Stern et al. .................... 606/33 |
| 5,373,849 A | 12/1994 | Maroney et al. | |
| 5,375,596 A | 12/1994 | Twiss et al. | |
| 5,377,678 A | 1/1995 | Dumoulin et al. | |
| 5,380,316 A | 1/1995 | Aita et al. ...................... 606/7 |
| 5,383,454 A | 1/1995 | Bucholz | |
| 5,383,874 A | 1/1995 | Jackson et al. ................ 606/1 |
| 5,383,923 A | 1/1995 | Webster, Jr. ................. 607/125 |
| 5,385,148 A | 1/1995 | Lesh et al. | |
| 5,389,096 A | 2/1995 | Aita et al. ..................... 606/15 |
| 5,391,199 A | 2/1995 | Ben Haim .................. 607/122 |
| 5,403,356 A | 4/1995 | Hill et al. ...................... 607/14 |
| 5,404,297 A | 4/1995 | Birk et al. ................... 362/421 |
| 5,409,004 A | 4/1995 | Sloan | |
| 5,423,321 A | 6/1995 | Fontenot | |
| 5,425,367 A | 6/1995 | Shapiro et al. | |
| 5,425,382 A | 6/1995 | Golden et al. .............. 128/899 |
| 5,429,132 A | 7/1995 | Guy et al. | |
| 5,431,168 A | 7/1995 | Webster, Jr. | |
| 5,433,198 A | 7/1995 | Desai | |
| 5,437,277 A | 8/1995 | Dumoulin et al. | |
| 5,443,489 A | 8/1995 | Ben-Haim .................. 607/115 |
| 5,450,846 A | 9/1995 | Goldreyer | |
| 5,465,717 A | 11/1995 | Imran et al. | |
| 5,471,982 A | 12/1995 | Edwards et al. | |
| 5,471,988 A | 12/1995 | Fujio et al. | |
| 5,480,422 A | 1/1996 | Ben-Haim .................. 607/122 |
| 5,483,951 A | 1/1996 | Frassica et al. ............. 600/104 |
| 5,487,391 A | 1/1996 | Panescu | |
| 5,538,008 A | 7/1996 | Crowe | |
| 5,554,152 A | 9/1996 | Aita et al. ...................... 606/7 |
| 5,555,883 A | 9/1996 | Avitall | |
| 5,558,091 A | 9/1996 | Acker et al. | |
| 5,558,092 A | 9/1996 | Unger et al. | |
| 5,577,502 A | 11/1996 | Darrow et al. | |
| 5,588,432 A | 12/1996 | Crowley | |
| 5,617,857 A | 4/1997 | Chader et al. | |
| 5,622,169 A | 4/1997 | Golden et al. | |
| 5,715,822 A | 2/1998 | Watkins et al. | |
| 5,729,129 A | 3/1998 | Acker ................... 324/207.12 |

FOREIGN PATENT DOCUMENTS

| | | |
|---|---|---|
| WO | WO 96/05768 | 2/1996 |
| WO | WO 96/41119 | 12/1996 |
| WO | WO 97/03609 | 2/1997 |
| WO | WO 97/29678 | 8/1997 |
| WO | WO 97/29679 | 8/1997 |
| WO | WO 97/29683 | 8/1997 |
| WO | WO 97/29684 | 8/1997 |
| WO | WO 97/29685 | 8/1997 |
| WO | WO 97/29701 | 8/1997 |
| WO | WO 97/29709 | 8/1997 |
| WO | WO 97/29710 | 8/1997 |
| WO | WO 97/29803 | 8/1997 |
| WO | WO 97/32179 | 9/1997 |

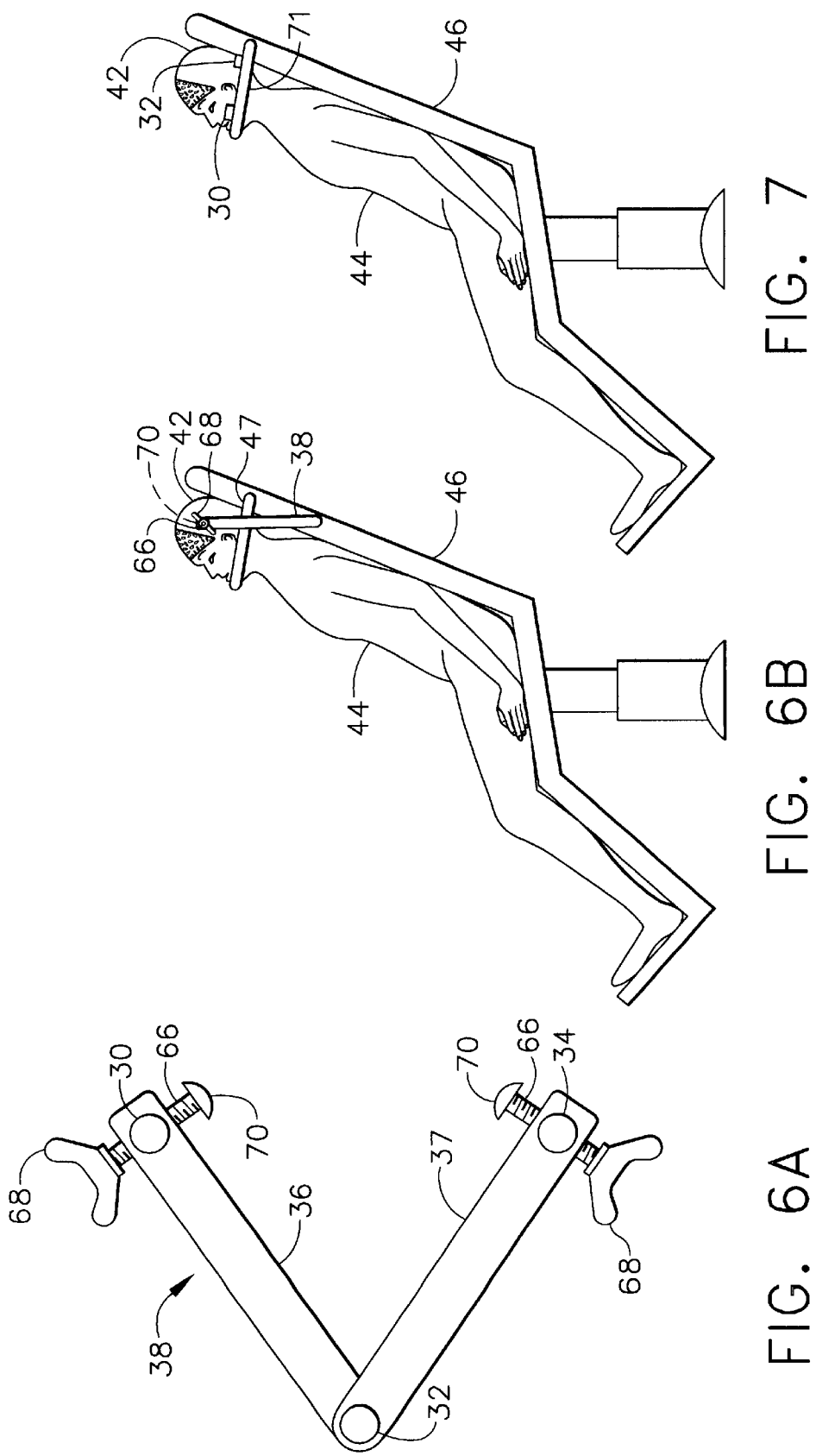

MOVABLE TRANSMIT OR RECEIVE COILS FOR LOCATION SYSTEM

CROSS-REFERENCE TO RELATED APPLICATIONS

The present application claims benefit of U.S. Provisional Application No. 60/012,241, filed Feb. 26, 1996 and U.S. Provisional Application No. 60/011,720, filed Feb. 15, 1996, the disclosures of which are hereby incorporated by reference herein.

The following PCT applications, each of which names Biosense, Inc. as an applicant, are also incorporated by reference herein: Catheter Bases Surgery filed on or about Feb. 14, 1997 in the Israeli Receiving Office; Intrabody energy Focusing field on or about Feb. 14, 1997 in the Israeli Receiving Office; Locatable Biopsy Needle, filed on or about Feb. 14, 1997 in the Israeli Receiving Office; Catheter Calibration and Usage Monitoring field on or about Feb. 14, 1997 in the Israeli Receiving Office; Precise Position Determination of Endoscopes filed on or about Feb. 14, 1997 in the Israeli Receiving Office; medical Probes with Field Transducers filed Feb. 14, 1997 in the United States Receiving Office; Catheter with Lumen filed Feb. 14, 1997 in the United States Receiving Office; Medical Procedures and Apparatus Using Intrabody Probes filed Feb. 14, 1997 in the United States Receiving Office; and Independently Positionable Transducers for Location System filed Feb. 14, 1997 in the United States Receiving Office. The PCT application entitled, Multi-Element Energy Focusing, filed Feb. 14, 1996 in the Israeli Receiving Office and naming Victor Spivak as applicant is also incorporated by reference herein.

TECHNICAL FIELD

The present invention relates to systems for medical diagnosis and treatment, and specifically to using reference field transducers and medical probes with probe field transducers to detect the position, orientation, or both of the probe within the body of a subject.

BACKGROUND ART

There are many medical procedures in which probes, such as catheters, are introduced into the body of a subject or patient. In procedures such as cardiac catherization and neurosurgery, it is often necessary for the physician or surgeon to know the location of the distal end of the probe inside the body. Although imaging methods such as fluoroscopy and ultrasound are sometimes used for this purpose, they are not always practical or desirable. For example, such systems typically require continuous imaging of the probe and patient during the procedure. In addition, fluoroscopic systems are often undesirable because that they expose the patient and physician to substantial ionizing radiation.

A number of locating systems for detecting the position of a probe or a catheter tip in the body of a patient have been proposed without the need for continuous imaging of the patient. These systems include, for example, those disclosed in U.S. Pat. Nos. 5,558,091; 5,391,199; 5,443,489; and International Patent Publications WO 94/04938 and WO 96/05768, the disclosures of which are hereby incorporated herein by reference. Other electromagnetic tracking systems, not necessarily for medical applications, are described in U.S. Pat. Nos. 3,644,825, 3,868,565, 4,017,858, 4,054,881 and 4,849,692.

Systems such as those disclosed in the '091, '199 and '489 patents and in the '768 publication determine the disposition (i.e., position, orientation, or both) of a probe using one or more fields transducers, such as a Hall effect devices, magnetoresistive devices, coils or other antennas carried on the probe. The transducers are typically located at or adjacent the distal end of the probe or at a precisely known location relative to the distal end of the probe. Such systems further utilize one or more reference field transducers disposed outside the body to provide an external frame of reference. The reference field transducers are operative to transmit or detect non-ionizing fields or field components such as magnetic field, electromagnetic radiation or acoustical energy such as ultrasonic vibration. By transmitting fields between the external reference field transducers and the probe field transducers, characteristics of the field transmissions between these devices can be determined and then used to determine the position and orientation of the probe in the external frame of reference.

As described, for example, in the aforementioned '091 patent, the frame of reference of the external field transducers can be registered with the frame of reference of imaging data such as magnetic resonance imaging data, computerized axial tomographic ("CAT") data, or conventional x-ray imaging data, and hence the position and/or orientation data derived from the system can be displayed can as a representation of the probe superimposed on an image of the patient's body. The physician can use this information to guide the probe to the desired location within the patient's body, and to monitor its location and orientation during treatment or measurement of the internal body structure. This arrangement greatly enhances the ability of the physician to navigate the distal end of the problem through bodily structures and offers significant advantages over conventional methods of navigating probes within the body by feel alone. Because it does not require acquiring an optical image of the surrounding tissues for navigation purposes, it can be used with probes which are too small to accommodate optical elements. These transducer-based systems also avoid the difficulties associated with navigation of a probe by continuous imaging of the probe and patient during the procedure and avoids, for example, prolonged exposure to ionizing radiation inherent in fluoroscopic systems.

Such systems typically utilize reference field transducers or coils which are provided in a fixed, immovable array, in locations such as on the ceiling of an operating room or rigidly fixed to operating or catherization table. In medical applications, where the system is used to track the location of a probe inside the body of a patient, the coil mounting may also interfere with free access by the physician to the patient.

For example, the aforementioned '768 publication describes a catheter system which uses a plurality of non-concentric coils adjacent to the distal end of the catheter. These coils generate signals in response to externally applied magnetic fields, which allow for the computation of six location and orientation coordinates, so that the disposition of the catheter is known without the need for simultaneous imaging. Preferably, three such coils or radiators are arrayed in fixed locations outside the body, adjacent to the area of the body into which the catheter is introduced. For example, in cardiac catherization, during which the patient is typically supine, three radiators are typically fixedly placed beneath the patient's thorax, in a fixed coplanar, triangular arrangement, with the centers of the coils from about 2 to 30 cm apart. Undesired movement of this array of radiators, however, can lead to errors in determination of the location or orientation of the catheter.

For detection of the position and orientation of catheters or probes inserted into the brain, the transducers or field radiating coils should desirably be positioned adjacent to the patient's head. In neurosurgery, however, the patient is often in a seated, upright position or else face-down. Thus, a triangular frame holding the three radiators as described above cannot be comfortably and stably positioned below the head. However, positioning the frame above or beside the head will generally interfere with the surgeon's manipulation of probes and surgical tools.

It would therefore be desirable to enhance the accuracy and efficacy of probe tracking systems as described above, and other types of systems involving application of electromagnetic or other non-ionizing energy field to a human body, by adjusting and optimizing the positions of the reference field transducers. As in the case of neurosurgery, optimal positioning may not be possible if the transducers are constrained in fixed position by a triangular or other mounting frame. For example, when a probe is to be tracked inside a patient's abdomen, it may be desirable to place radiators in fixed, known positions around the circumference of the abdomen, rather than under the patient's back.

In addition, it would be desirable to provide greater flexibility as to where the transducers are placed about the subject. Such increased placement flexibility would allow the physician to have easier access to the patient. Flexibility over placement of the transducers would allow custom positioning of the transducers to move them to the closest possible location to increase sensitivity of the locating system.

DISCLOSURE OF THE INVENTION

The present invention addresses the need of providing greater flexibility in the positioning of position determining transducers by providing a system for determining the disposition of a probe within the body of a patient, comprising a probe having one or more probe field transducers mounted therein and one or more reference field transducers mounted on a frame. The system includes means for mounting the frame for movement relative to the patient so that the reference field transducers can be selectively positioned in different positions in close proximity to the body of the patient. The mounting means may desirably comprise a flexible, goose neck arm.

Transmission means are provided to transmit one or more non-ionizing fields between the probe field transducers and the reference field transducers and detection means detect each such transmitted field. Finally, calculation means determine the relative disposition of said probe with respect to said reference field transducers from properties of the detected fields and from the relative dispositions of said reference field transducers with respect to one another.

In preferred embodiments, two or more reference field transducers are provided and the frame incorporates a linkage so as to allow each of said reference field transducers to be movable in a known spatial relationship with respect to one another.

In other preferred embodiments, translation means, such as one or more fiducial transducers attached to the body of the patient, translate the disposition of said probe relative to said reference field transducers to a known deposition relative to the body of the patient.

In a method in accordance with a preferred embodiment of the present invention, the disposition of a probe within the body of a patient is determined by the steps of: (a) providing a probe having one or more probe field transducers mounted therein; (b) providing one or more reference field transducers mounted on a frame having means for mounting the frame for movement relative to the patient so that the reference field transducers can be selectively positioned in different positions in close proximity to the body of the patient; (c) adjusting the frame so that said reference field transducers are positioned in a first location in close proximity to the body of the patient; (d) transmitting one or more non-ionizing fields between the probe field transducers and the reference field transducers; (e) detecting each such transmitted field; and (f) calculating the relative disposition of the probe with respect to the reference field transducers from properties of the detected fields and from the relative dispositions of the reference field transducers with respect to one another.

In a preferred method, the present invention further includes the step of translating the disposition of the probe relative to the reference field transducers to a known disposition relative to the body of the patient. Preferably, the translation step includes comprises attaching one or more fiducial transducers to the body of the patient and detecting non-ionizing fields transmitted between the reference field transducers and the fiducial transducers.

It is also an object of the present invention to provide a stable frame to hold reference field transducers for use in determining the disposition of a probe inside the body of a subject during a medical or surgical procedure. In one aspect of the present invention, the frame is suitable for positioning the reference field transducers in close proximity to the subject's head without interfering with neurosurgical procedures.

A further object of the present invention is that the frame may be quickly and conveniently fixed in a desired position for optimal transmission of non-ionizing fields into a part of the subject's body, preferably surrounding the part of the body, and quickly removed from the position thereafter.

In preferred embodiments of the present invention, apparatus for generating non-ionizing energy fields, useful for determining the disposition of a probe inside the body, comprises two or more reference field transducers fixed to a rigid frame of a shape that allows the transducers to be positioned stably in an optimal location in close proximity to a part of the body into which the probe is inserted, so as to allow accurate determination of the disposition of the probe. In preferred embodiments of the present invention, the reference field transducers are radiator coils which generate electromagnetic fields.

In some preferred embodiments of the present invention, the apparatus for generating non-ionizing fields comprises three transducers or coils fixed to a rigid frame. Preferably the frame is conveniently and stably positioned below the thorax or abdomen during insertion of probes therein. In other preferred embodiments of the present invention, for use in neurosurgery, the apparatus for generating fields comprises three coils fixed to a frame below the head, in close proximity to the head. Preferably the frame includes an opening that is adapted to fit around the head or neck.

More generally, in preferred embodiments of the present invention, three or more co-planar reference field transducers define a polygonal shape, wherein the transducers correspond to the vertices of the polygon. A section of the frame corresponding to the side of the polygon is open, and the frame is positioned so that a part of the body is partly contained in this open section. The frame may comprises a mounting bracket, which couples rigidly to the operating table, bed or other apparatus used for fixing the subject's position.

In some preferred embodiments of the present invention, the frame couples to apparatus for fixing the position of a subject's head during neurosurgery. In one such preferred embodiment, one or more reference field transducers are fixed to the head fixing apparatus. Electromagnetic fields generated by the transducers cause them to generate position-responsive electrical signals, which are analyzed in order to determine and verify the position of the apparatus relative to the frame. Furthermore, in some such preferred embodiments of the present invention the frame or the head fixing apparatus further include predetermined, known locations, which are marked on the frame or head fixing apparatus, wherein a probe for insertion into the body is first placed in these locations for calibration and reference positioning.

Additionally, in some preferred embodiments of the present invention, the mounting bracket includes a fixable joint, which allows the angular orientation of the frame relative to the bed or relative to the head fixing apparatus to be adjusted and then rigidly fixed at a desired angle. In some preferred embodiments, the frame comprises one or more adjustment hinges. Each such hinge may be flexed so as to adjust the angle between two sides of the frame adjacent thereto, and then fixed rigidly at the desired angle.

In some preferred embodiments of the present invention, the frame comprises head rest fixtures. The positions of these fixtures may be adjusted so that the fixtures fit snugly against the head, so as to maintain the head in a fixed position relative to the reference field transducers and prevent motion of the head relative to the frame.

There is therefore provided in accordance with a preferred embodiment of the present invention, apparatus for generating non-ionizing fields inside the body of a subject, comprising a plurality of reference field transducers, which generate non-ionizing fields, and a rigid frame to which the transducers are fixed. The rigid frame is constructed so as to allow the reference field transducers to be fixably positioned in close proximity to the body. Preferably, the transducers define a polygon, and the frame is constructed so as to be positionable so that an axis perpendicular to the plane of the polygon and passing through the its center passes through the body. Furthermore, the frame is preferably constructed so as to be positionable so that a part of the body is substantially inside the polygon.

Preferably, the frame includes a mounting bracket, which couples rigidly to an operating table or bed. The mounting bracket preferably includes a fixable joint, which is constructed so as to allow the frame to be adjusted and fixed at a desired angle relative to the operating table or bed. Furthermore, the frame may preferably include a plurality of arms and an adjustment hinge, which couples two or more of the arms and is constructed so as to allow the angle defined by the two or more arms that it couples to be adjusted and fixed rigidly in a desired position.

Preferred embodiments of the present invention provide that the frame be adapted so that the reference field transducers are fixably positioned in close proximity to the head and generate non-ionizing fields in a vicinity of the head. Preferably the frame is mechanically coupled to apparatus for fixing the position of the head during surgery. Alternatively the frame may be adapted to fix the position of the head during surgery. The frame may further comprise head engaging elements, which bear against opposite sides of the head. Preferably, the transducers are coils which generate magnetic fields.

There is further provided in accordance with a preferred embodiment of the present invention, a system for determining the position and orientation of a probe inside the body of a subject, including apparatus for generating fields, as described above; a probe for insertion into the body; and at least one device responsive to the fields for determining position and orientation coordinates of the probe. Preferably, this system includes one or more position sensing devices, preferably fixed to the probe, and adapted so to allow the positions of the transducers to be determined. Preferably the fields are magnetic fields, and the field responsive device is a coil. Also, the frame preferably further includes probe calibration receptacles.

Further preferred embodiments of the present invention include apparatus for generating non-ionizing fields in the vicinity of the head of a human medical patient, which such apparatus includes one or more reference field transducers and a rigid frame to which the transducers are fixed. The frame has an opening therein in which the head can be located such that the frame is in close proximity to and at least partially encircles a portion of the head or neck of the patient.

The frame preferably comprises a pair of arm members defining a triangle having two closed sides and an open side such that a portion of the head or neck can be readily positioned within the frame through the open side. Preferably, transducers are positioned at at least the three corners of the frame and the arm members of the frame are hingedly connected to one another. Further, means for measuring the relative displacement between the arm members can be provided.

In other preferred embodiments, the head clamp may be attached to the frame to prevent movement of the head. In another preferred arrangement, the frame may be integrally formed with a head clamp to prevent movement of the head. In other preferred embodiments, the frame may further include head engaging fixtures adjustable to tighten to the head.

BRIEF DESCRIPTION OF THE DRAWINGS

FIG. 6A is a schematic representation of a frame in accordance with another preferred embodiment of the present invention;

FIG. 6B shows the frame of FIG. 6A in use during neurosurgery;

FIG. 7 is a schematic representation of a frame in accordance with yet another preferred embodiment of the present invention;

BEST MODES FOR CARRYING OUT THE INVENTION

Figure 1:
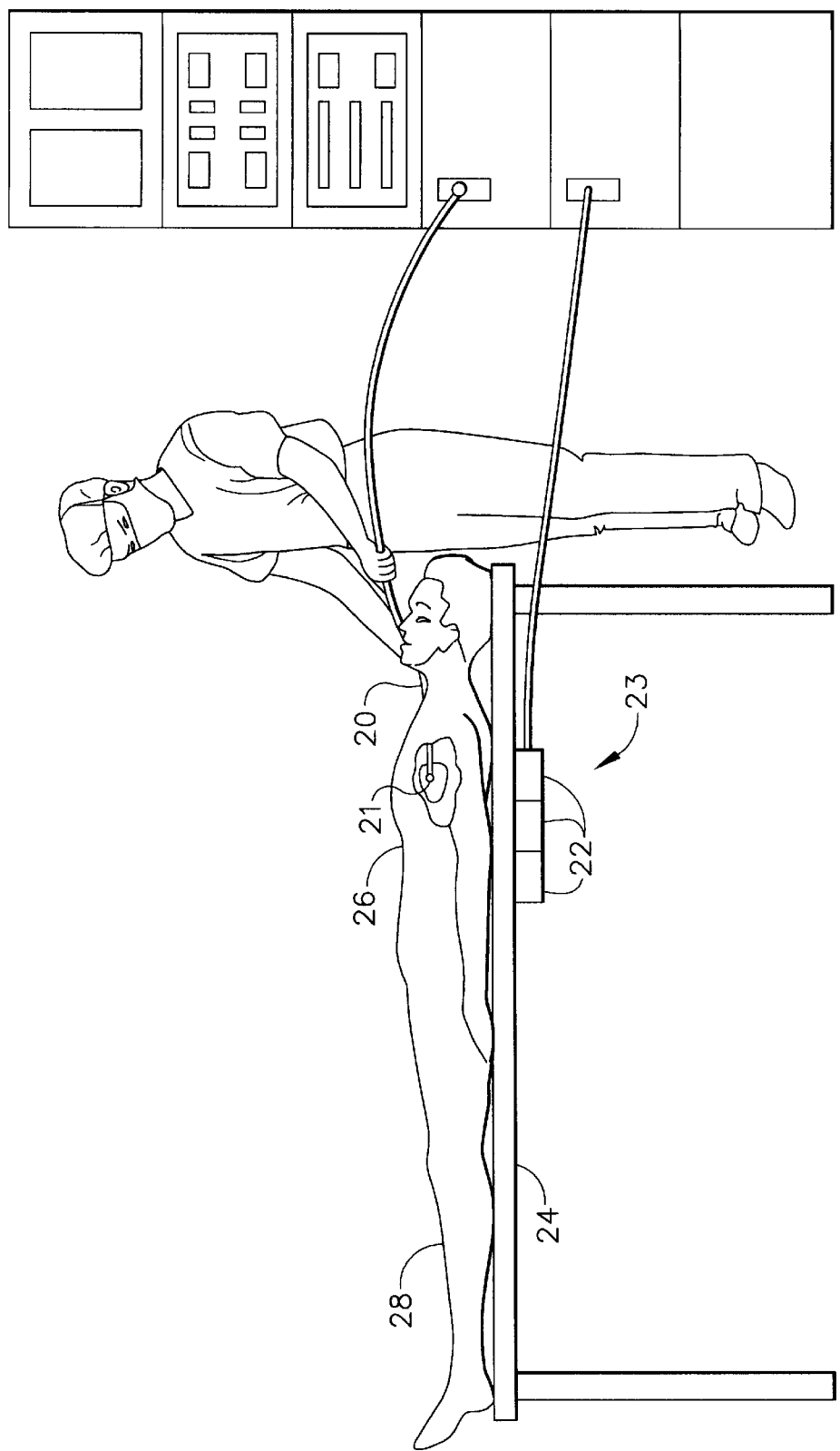
FIG. 1 shows a preferred embodiment of the present invention in use during cardiac catherization.

FIG. 1 shows a system for determining the position, orientation, or both of a probe, such as a catheter 20, disposed inside the body of a subject in use during a cardiac catherization procedure, in accordance with a preferred embodiment of the present invention.

Preferably the system is of a type described in the '768 publication, which is assigned to the assignee of the present patent application and whose disclosure is incorporated herein by reference. The system includes means for generating the disposition of the distal end of the probe or catheter 20. As used in this disclosure, the term "disposition" refers to the position, the orientation, or both of the probe or transducer.

Here, the probe includes a plurality of transducers in the form of non-concentric receiver coils 21 (only one being shown) adjacent to a locatable site in the catheter, for example near its distal end. These coils generate signals in response to magnetic fields generated by reference field transducers 22, fixed to a frame 23, which is in turn fixed to operating table 24 beneath thorax 26 of subject 28. The signals allow for the determination of six location and orientation coordinates, so that the disposition of catheter 20 is known without the need for simultaneous imaging.

It will be understood that although this and other preferred embodiments of the present invention are described with reference to systems for determination of six-dimensional disposition, the present invention is equally applicable to systems that determine one-, two-, three-, four- or five-dimensional location and orientation coordinates.

Figure 2:
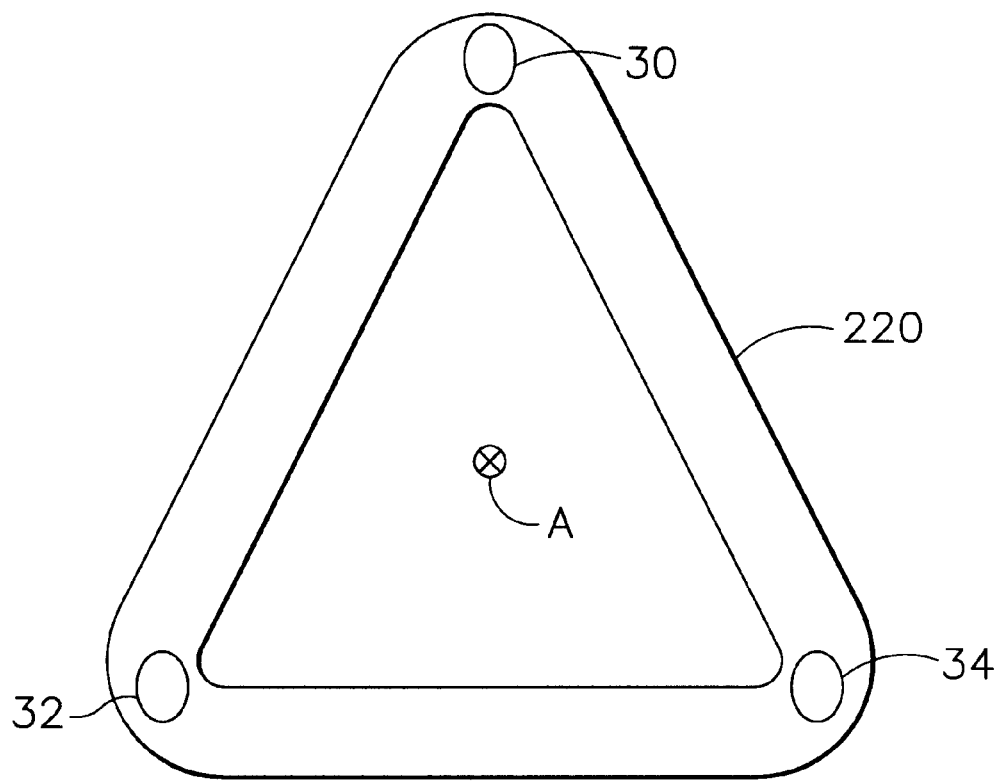
FIG. 2 is a schematic representation of a frame to which field transducers are mounted in accordance with the preferred embodiment of the present invention whose use is shown in FIG. 1.

FIG. 2 shows a schematic view of one aspect of the present invention which comprises a frame 220, to which three reference field transducers 30, 32 and 34 are fixed, in accordance with a preferred embodiment of the present invention. Frame 220 is preferably made of hard plastic or other rigid material and so mounted as to prevent motion of the reference field transducers during the catheterization or other medical procedure. Transducers 30, 32 and 34 are preferably field generating coils, which generate a multiplicity of distinguishable AC magnetic fields when driven by field generating circuits (not shown in the figure). It will be appreciated by those skilled in the art that the respective magnetic fields generated by transducers 30, 32 and 34 will be approximately equal and maximal amplitudes in a region adjacent to an axis A that passes through the center of the triangle defined by the transducers and is perpendicular to the plane thereof. Empirically it has been found that the position of the probe and hence the catheter is determined with greatest accuracy in this region.

In preferred embodiments of the present invention, the magnetic fields generated by transducers 30, 32 and 34 are distinguishable by virtue of having different AC frequencies. Preferably the transducers are coils, which are driven by drive circuitry (not shown in the figures) at respective resonant frequencies thereof and generate magnetic fields having substantially equal amplitudes at these frequencies. As is known in the art, given two resonant coils of respective diameters $D_1$ and $D_2$, and respective frequencies $\omega_1$ and $\omega_2$, if $\omega_1 > \omega_2$ and both coils are driven at equal levels of input power, then $D_2$ must generally be greater than $D_1$ in order that the amplitudes of the magnetic fields at the respective frequencies $\omega_1$ and $\omega_2$ be substantially equal. Therefore, transducers 30, 32 and 34 are preferably of different diameters, as shown, for example, in FIG. 8A, with the coil whose resonant frequency is largest having the smallest diameter, and vice-versa.

In preferred embodiments of the present invention, transducers 30, 32 and 34 are fixed to frame 220 so as to define an isosceles triangle. Preferably this triangle is not equilateral, but rather has an apex that is more acute than the other two vertices, so that the frame may fit easily under operating table 24 (FIG. 1) without protruding at the sides. Preferably, for the same reason, the largest of the coils is positioned at the apex of the triangle.

Although FIG. 2 shows a triangular frame 220 and three transducers 30, 32 and 34, other preferred embodiments of the present invention may comprise two, four or more transducers. Furthermore, the frame to which the transducers are fixed may be of some other polygonal or non-polygonal shape, which may be planar or non-planar, so long as the shape of the frame is such as to allow the transducers to be stably positioned adjacent to the portion of the body where the probe is located. Preferably, the frame is positioned and oriented so that the portion of the body where the probe is located is adjacent to a central axis defined by the positions of the transducers. The term center and central in this context are taken to refer to the center of an equilateral polygon, if the transducers define such a geometrical figure, or to the geometrical center of mass of a figure defined by the transducers, as determined according to methods known in the art.

Figure 3:
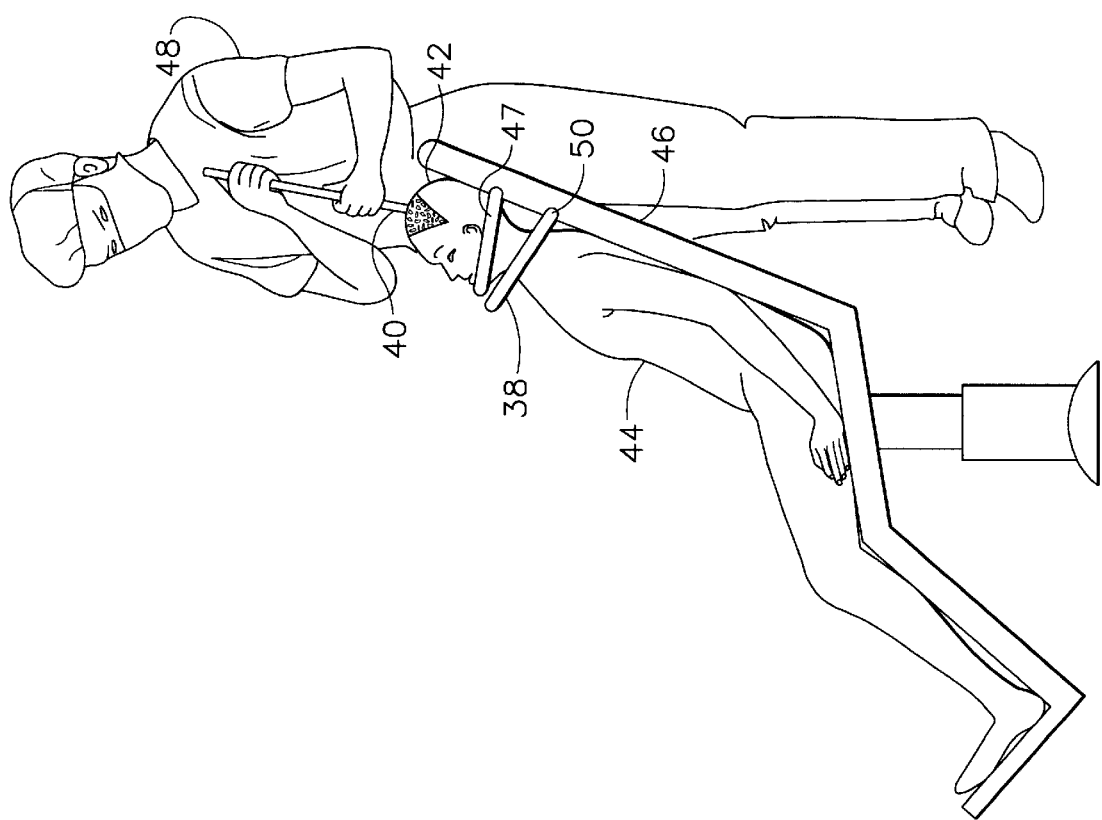
FIG. 3 shows a preferred embodiment of the present invention in use during neurosurgery.

In another preferred embodiment of the present invention, shown in FIG. 3, a system for determining disposition of a probe, preferably a catheter 40, inside the head 42 of a subject 44, is used during neurosurgery. Preferably the system is of a type described in the above mentioned '103 PCT patent application, although the preferred embodiment of the invention shown in FIG. 3 is equally applicable to other types of systems for determining probe disposition. Frame 38 holds reference field transducers 30, 32 and 34 (FIG. 4) adjacent to the head 42 of subject 44.

Figure 4:
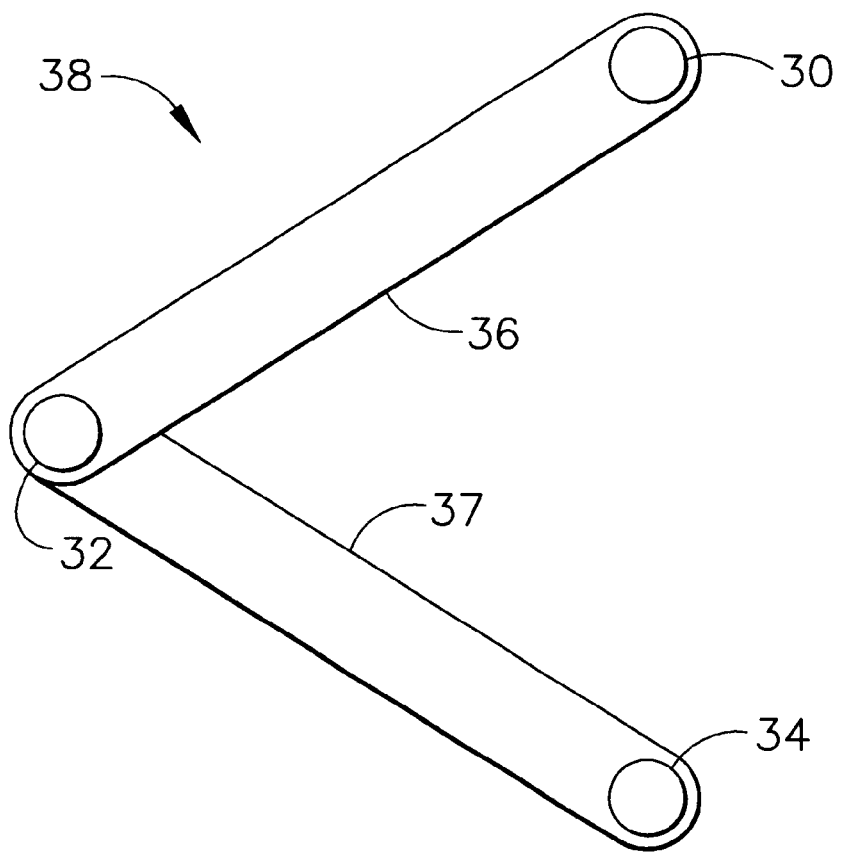
FIG. 4 is a schematic representation of a frame to which field transducers are mounted in accordance with the preferred embodiment of the present invention whose use is shown in FIG. 3.

As shown in FIG. 4, in a preferred embodiment of the present invention, frame 38 comprises rigid arms 36 and 37, which form two sides of a triangle. Arms 36 and 37 are preferably made of hard plastic or other rigid material. The third side of the triangle is open, so that the rear portion of head 42 of patient 44 can be positioned in the space between arms 36 and 37, as shown in FIG. 3. In this way transducers 30, 32 and 34 are positioned so that head 42 is located within the region wherein the position of catheter 40 may be determined most accurately, as explained above.

Figure 5:
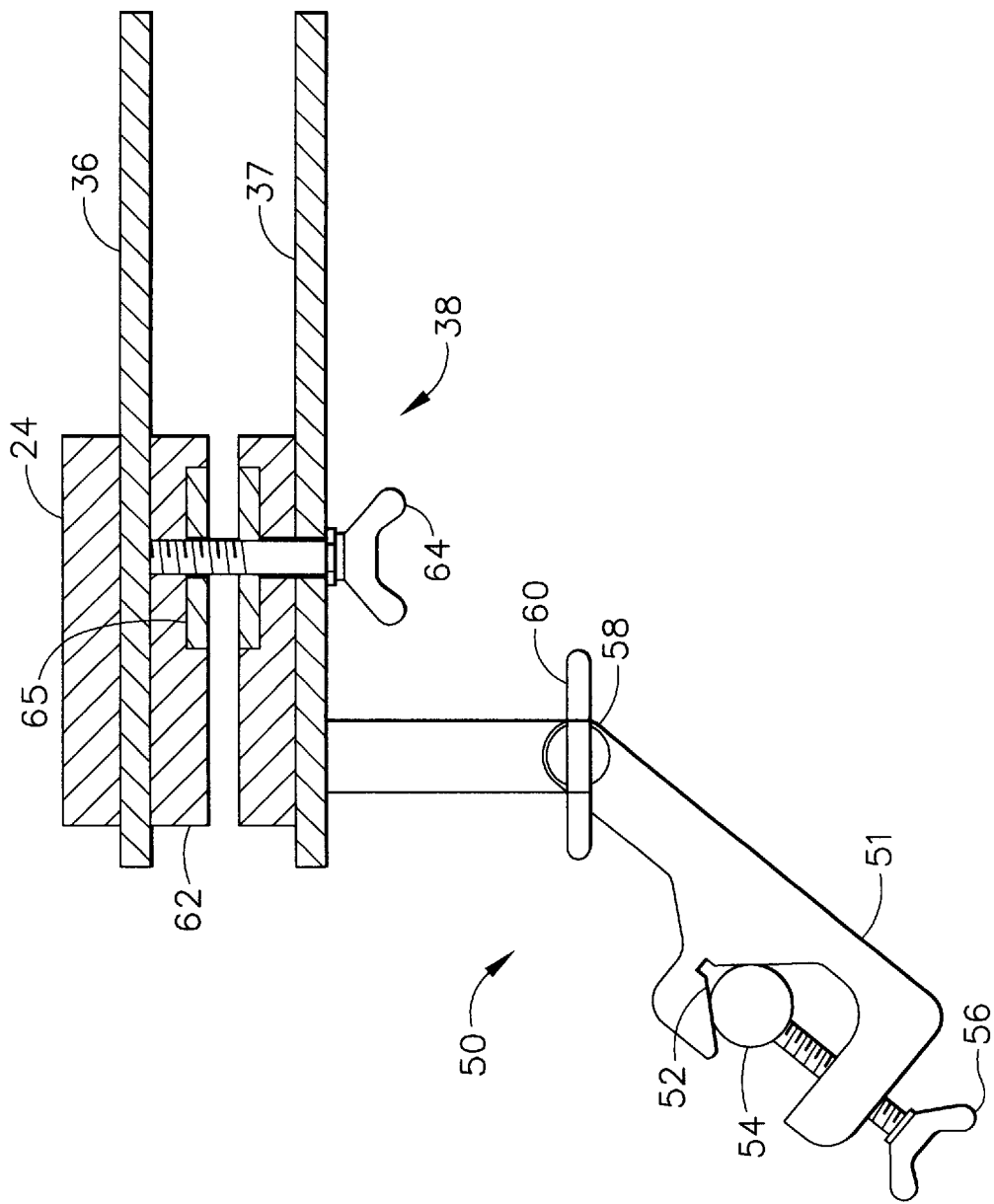
FIG. 5 is a sectional view showing details of a hinge, joint and mounting bracket in accordance with a preferred embodiment of the present invention.

Referring also to FIG. 5, frame 38 may be fixed by a mounting bracket 50 to operating table 46 (FIG. 3), which is positioned so as to maintain the patient in a sitting position during surgery. Head clamp 47 is fixed to table 46 and is fastened tightly to head 42 so as to prevent motion of the head. It will be appreciated that surgeon 48 is free to operate on the front portion of head 42, unhampered by frame 38.

Details of a preferred embodiment of mounting bracket 50 are shown in sectional view in FIG. 5. Preferably bracket 50 comprises a clamp 51 with a groove 52 that engages rail 54, which is rigidly attached to table 46. A thumbscrew 56 is tightened against rail 54 to hold the bracket in the desired position. Bracket 50 is coupled to frame 38 by a fixable joint 58, which is preferably a ball joint. After joint 58 has been positioned at the desired angle, thumbscrew 60 is tightened to hold joint 58 rigidly in position.

Furthermore, in the preferred embodiment of the present invention shown in FIG. 5, adjustable hinge 62 allows the angle between arms 36 and 37 of frame 38 to be adjusted. After the arms are set to the desired angle, thumbscrew 64 is tightened to prevent further motion of the hinge. Hinge 62 preferably includes a rotation measuring device 65, of a type known in the art, such as an optical encoder device, which allows the angle between arms 36 and 37 to be accurately determined, so that the relative positions of transducers 30, 32 and 34 are known.

Similarly, other preferred embodiments of frames to which transducers are fixed in accordance with the present invention may include hinges or joints that allow angles and the displacement between arms of the frames to be varied, so as to position the transducers optimally in proximity to a part of the body of a subject, for accurate determination of the position of a probe therein. Frames in accordance with these embodiments may preferably include means, known in the art, for measurement of the angles and displacement between the arms of the frames.

While as explained above, the relative positions of the transducers with respect to one another can be determined through geometric methods such as by measuring the angles between the transducers or displacement of the arms which carry the transducers, other methods may be used. For instance, as disclosed in the application entitled "Independently Positionable Transducers For Location System" filed on even data herewith and assigned to the assignee of the present application, one or more calibration field transducers can be provided in association with each reference field transducer. The calibration transducers determine the relative positions of the field transducers with respect to one another after they are located in their desired positions by the transmitting and detecting non-ionizing fields between the calibration and reference field transducers. In one such preferred embodiment, a device for generating position information is placed adjacent to each of the transducers on the frame, thereby allowing the relative positions of the transducers to be accurately determined. These devices for generating position information may, for example, comprise transducers such as sensor coils, which generate position-responsive electrical signals in response to externally-applied magnetic fields, and which signals are analyzed in order to determine the position of the apparatus relative to the frame.

In some preferred embodiments of the present invention, as shown in FIGS. 6A and 6B, frame 38 includes head engaging fixtures 70 at the ends of arms 36 and 37 that are adjacent to the head. Fixtures 70 are adjusted and tightened so as to bear firmly against opposite sides of the head, for example by turning thumbscrews 68 to advance threaded rods 66, coupled to fixtures 70, through respective threaded holes in arms 36 and 37. Thus, transducers 30, 32 and 34 are maintained in fixed positions relative to the head during the entire surgical operation. Furthermore, in this embodiment frame 38 may also be useful in holding head 42 in a desired orientation relative to operating table 46, in conjunction with head clamp 47.

In another preferred embodiment of the present invention, shown in FIG. 7, transducers 30, 32 and 34 are fixed to a rigid head clamp 71, which thereby serves as the frame for mounting the radiators in accordance with the invention. Head clamp is preferably fastened to the patient's head in a similar manner to head clamp 47, shown in FIG. 3.

Figure 8A:
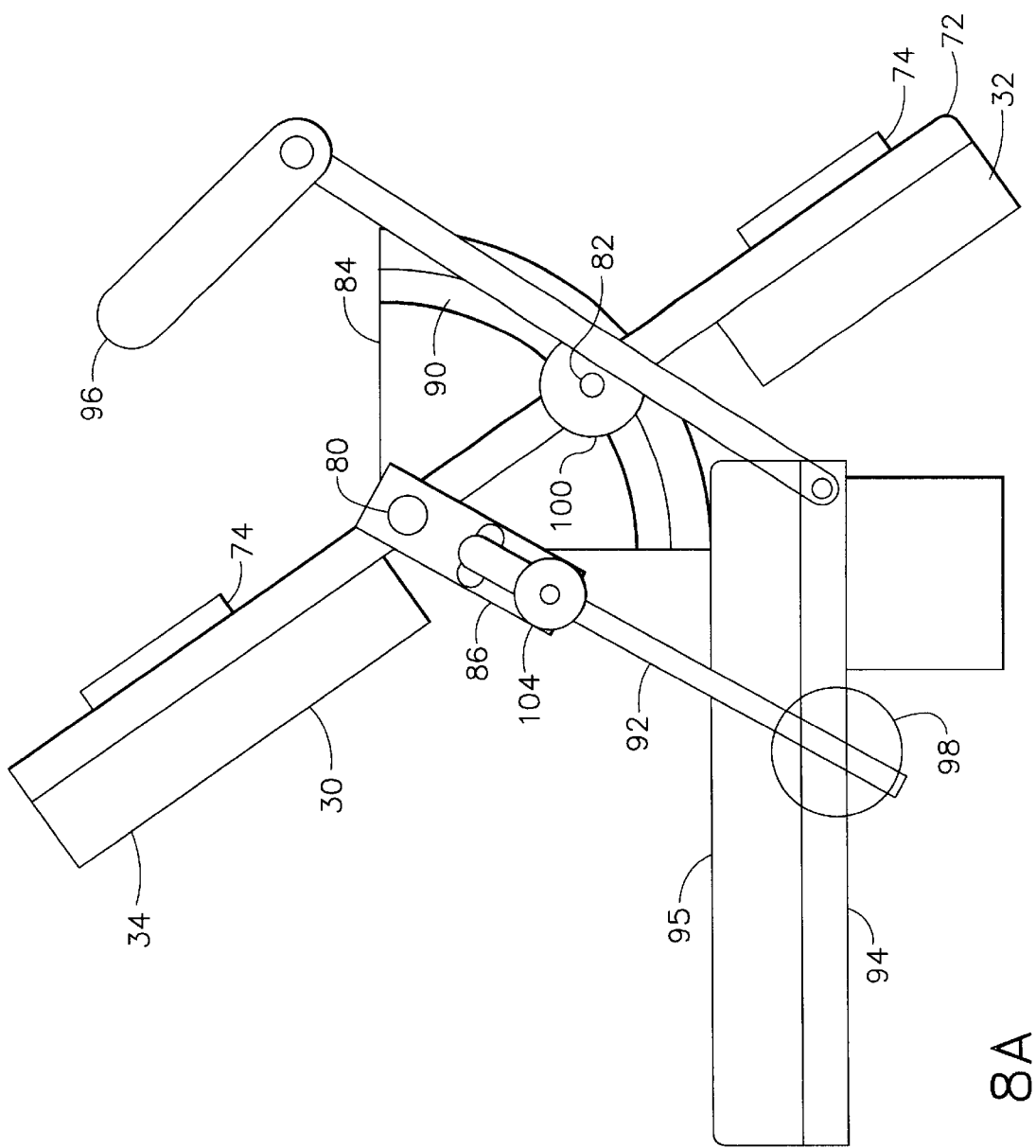
FIG. 8A is a schematic representation of a frame in accordance with still another preferred embodiment of the present invention.
Figure 8B:
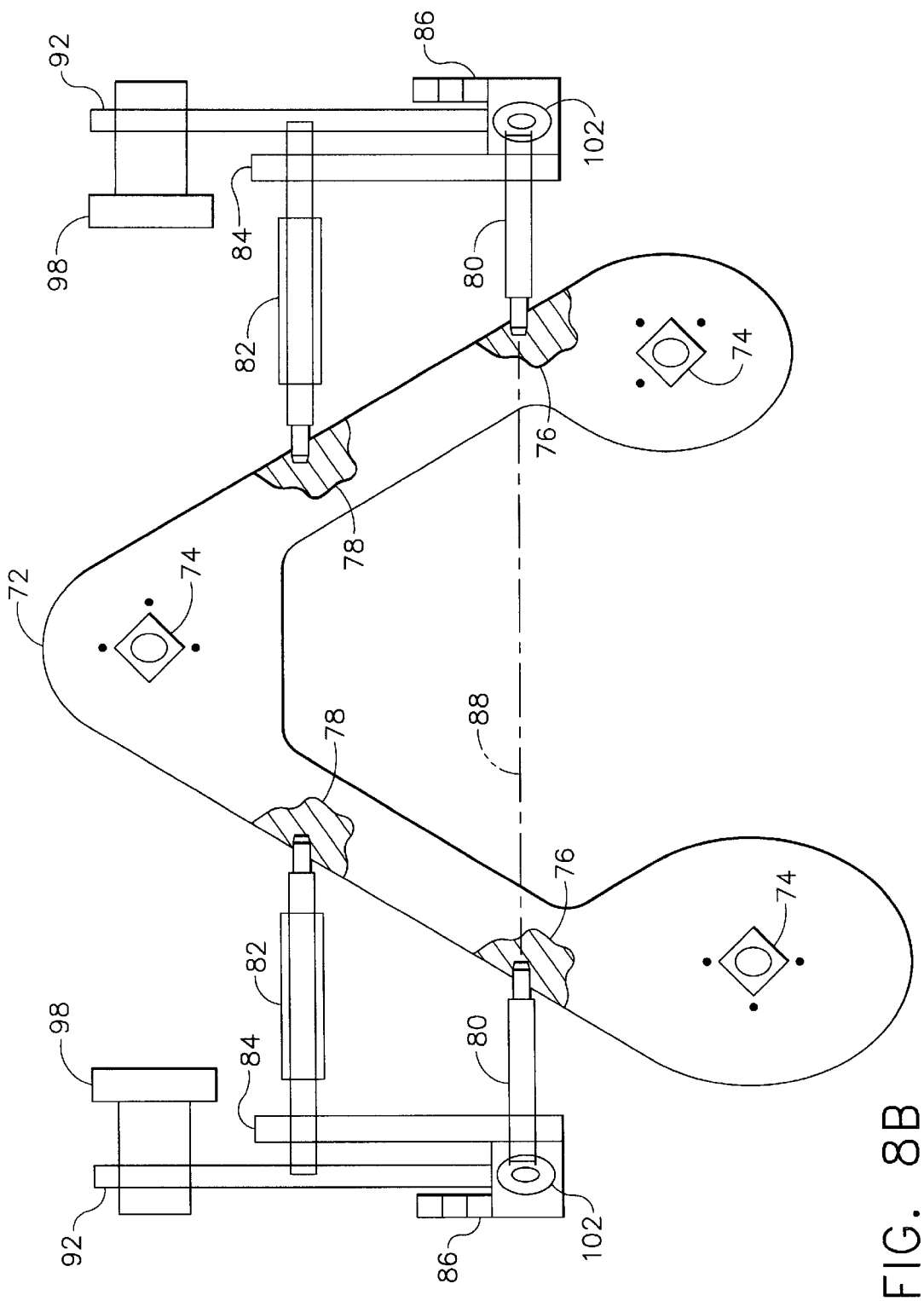
FIG. 8B is a schematic top view of the preferred embodiment of FIG. 8A.

FIGS. 8A and 8B show another preferred embodiment of the present invention, useful in ensuring that the positions of transducers 30, 32 and 34 are securely fixed, and will not move in the course of the surgical operation. FIG. 8A shows a frame 72 attached to an operating table 94. Frame 72 includes mounts 74 to which transducers 30, 32 and 34 are fixed. As shown in FIG. 8B, frame 72 further comprises two pairs of pin receptacles 76 and 78 on opposing sides of the frame, which are engaged by hinge pins 80 and guide pins 82 respectively. Frame 72 may be made of a single, rigid piece of material, which is preferably plastic.

Hinge pins 80 engage holes in guide rings 84 and in holders 86 on both sides of frame 72, so that the frame may rotate about an axis 88 defined by the pair of pins 80, as shown in FIG. 8B. Guide pins 82 engage slots 90 of guide rings 84, so that as frame 72 rotates about axis 88, pins 82 slide along the slots. Holders 86 are engaged by rods 92, which couple frame 72 and guide rings 84 to operating table 94.

In preparation for a surgical procedure in accordance with the preferred embodiment of FIGS. 8A and 8B, a subject lies on mattress 95 of operating table 94, with his head in contact with a clamped firmly to head support 96, whose details are not shown in the figure. Frame 72 is rotated about axis 88 so as to position radiators fixed to mounts 74 in the desired positions adjacent to the head. Knobs 98, 100, 102 and 104 are then tightened to hold frame 72 rigidly in the desired orientation. Knobs 98 and 104 together prevent motion of rods 92, while knobs 100 (FIG. 8A) tighten guide pins 82 in slots 90, and knobs 102 prevent rotation of hinge pins 80 in holders 86. This redundancy of tightening knobs ensures that frame 72 will not move accidentally.

Figure 9:
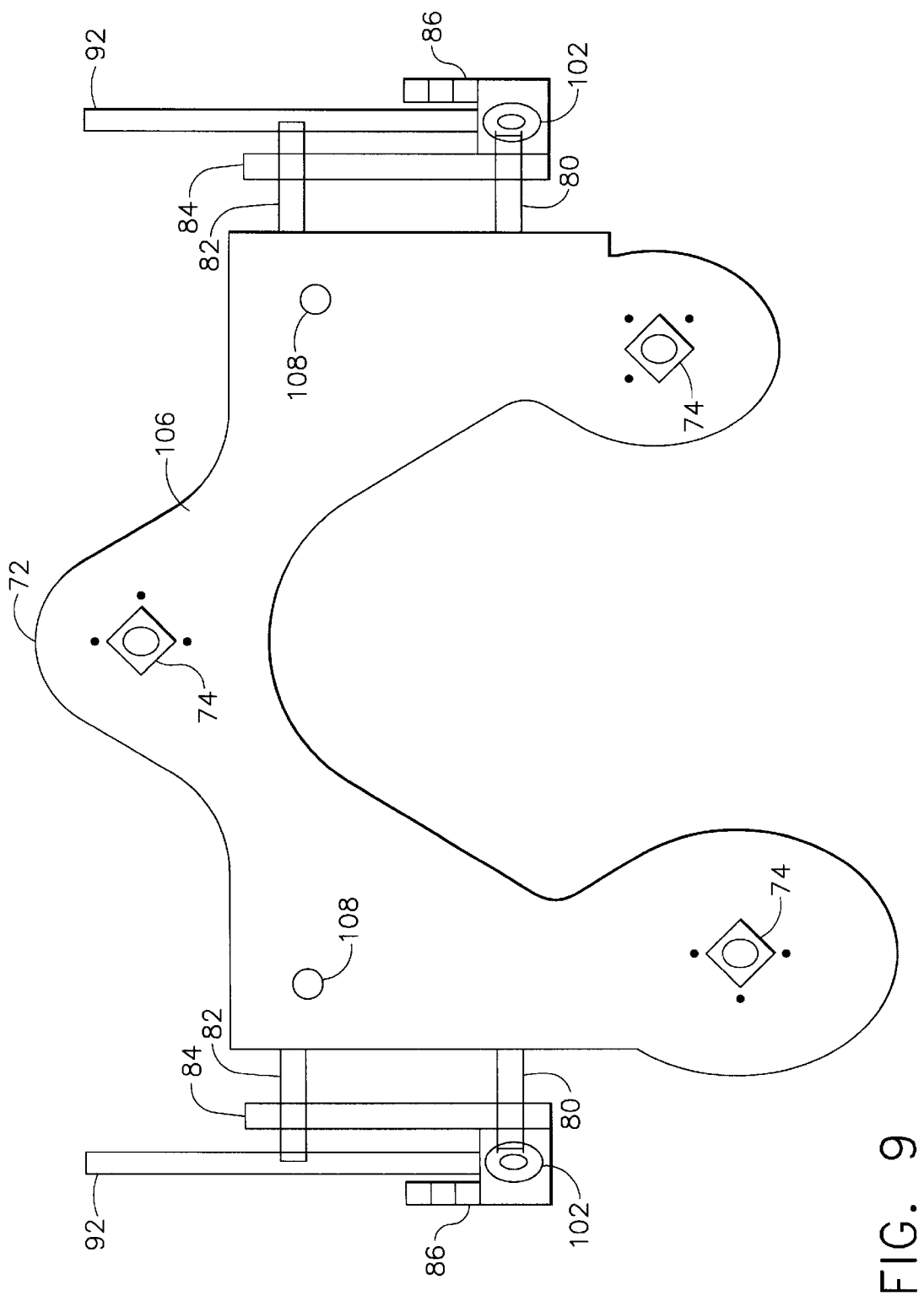
FIG. 9 is a schematic representation of an alternative preferred embodiment of the present invention.

FIG. 9 shows an alternative preferred embodiment of the present invention, wherein frame 106 is identical in operation to frame 72 shown in FIGS. 8A and 8B. In the embodiment shown in FIG. 9, however, the portion of frame 106 that engages pins 80 and 81 is made wider, so that the frame will hold its position relative to table 94 with greater rigidity when fixed by tightening knobs 98, 100, 102 and 104.

Frame 106 further includes catheter calibration receptacles 108, positioned in known locations relative to transducers mounts 74. Preferably, before a probe carrying catheter is inserted into the body of a subject, the catheter is calibrated by placing the distal tip thereof, which carried the probe, in each of receptacles 108 in turn, and comparing the respective known position of the receptacle with position information derived from signals generated by position information generating means in the catheter, as described above.

The calibration data derived from this procedure may be used in conjunction with calibration data stored in the catheter, as described in an unpublished U.S. Provisional patent application No. 60/017,634 by Osadchy, Fried and Ben-Haim, entitled, "Catheter Calibration System," and filed on May 17, 1996, which is assigned to the assignee of the present patent application, and whose disclosure is incorporated herein by reference.

The above preferred embodiments have been described with respect to their use in neurosurgery. It will be appreciated, however, that other embodiments of the present invention may be useful in a tracking the position of a probe or catheter inside other portions of the body, under which a closed, polygonal frame cannot be conveniently and stably positioned during surgery. Still other preferred embodiments of the present invention are useful when, for optimal tracking performance, it is desirable to position transducers around, rather than under, the portion of the body in question.

Figure 10:
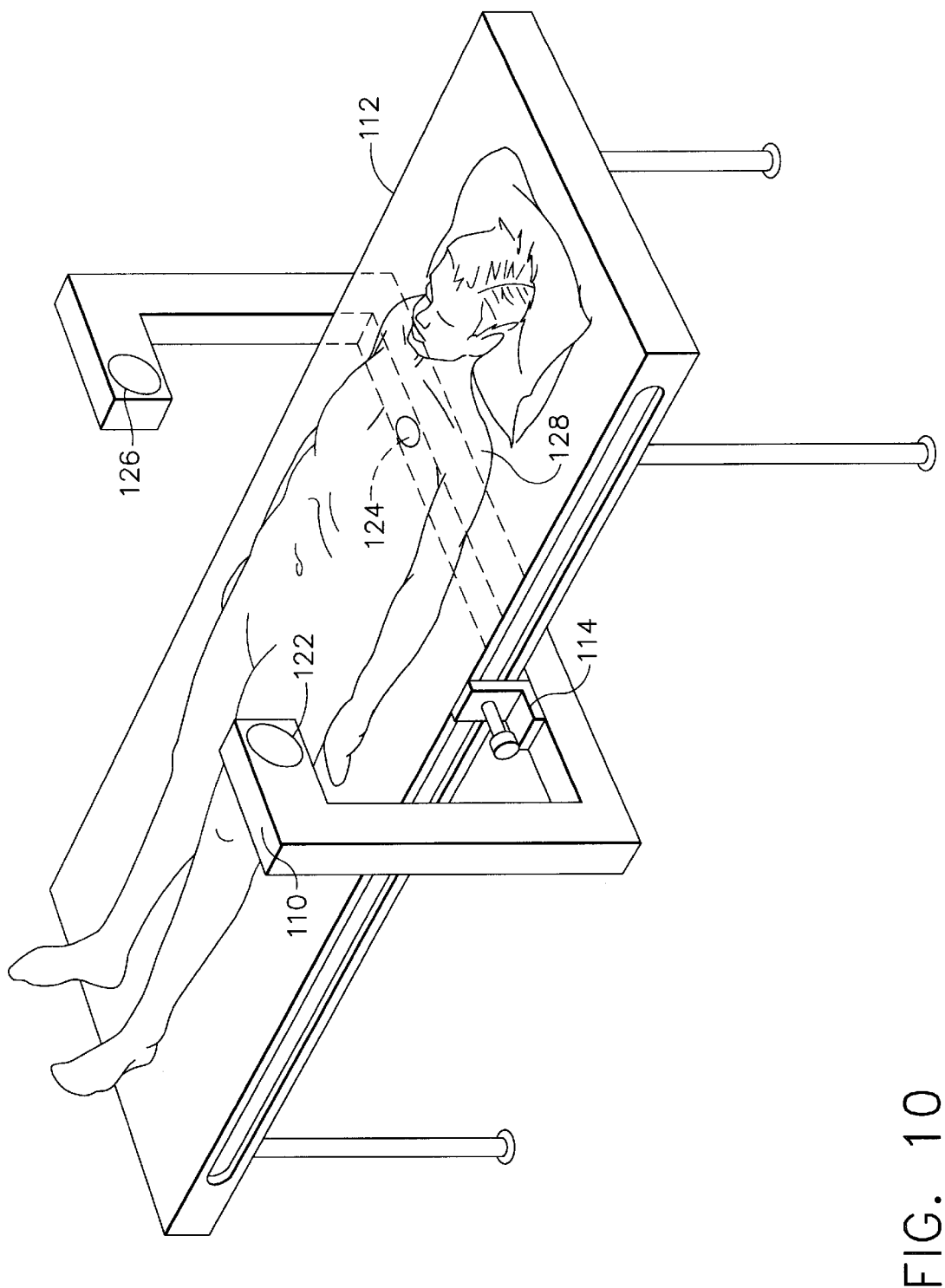
FIG. 10 is a perspective view of a further preferred embodiment of the present invention, for use in abdominal or thoracic surgery.

Thus, in a preferred embodiment of the present invention shown in FIG. 10, a U-shaped frame 110 provides a stable mount for transducers 122, 124 and 126 attached thereto, which may be used as part of a system for tracking a probe inside the abdomen of the patient 128. Frame 110 allows transducers 122 and 126 to be positioned above the left and right sides of the abdomen respectively, while transducer 124 is positioned below the back. Frame 110 is connected to operating table 112 by mounting mechanism 114, which is similar in function and construction to mounting bracket 50, as shown in FIG. 5. Mechanism 114 allows the frame to tilt from side to side and to be suitably slid back and forth along the length of table 112, until it is locked in the desired position.

It will be further appreciated that although aspects of the above preferred embodiments have been described with reference to a system for position determination based on magnetic fields, the present invention is equally applicable to other types of position determination system known in the art, such as systems that use other forms of field transducers, such as those which radiate and detect acoustic, optical or ultrasonic fields. The present invention will generally be useful in other systems for medical use in which radiation fields are transmitted into or received from the body of subject.

Figure 11A:
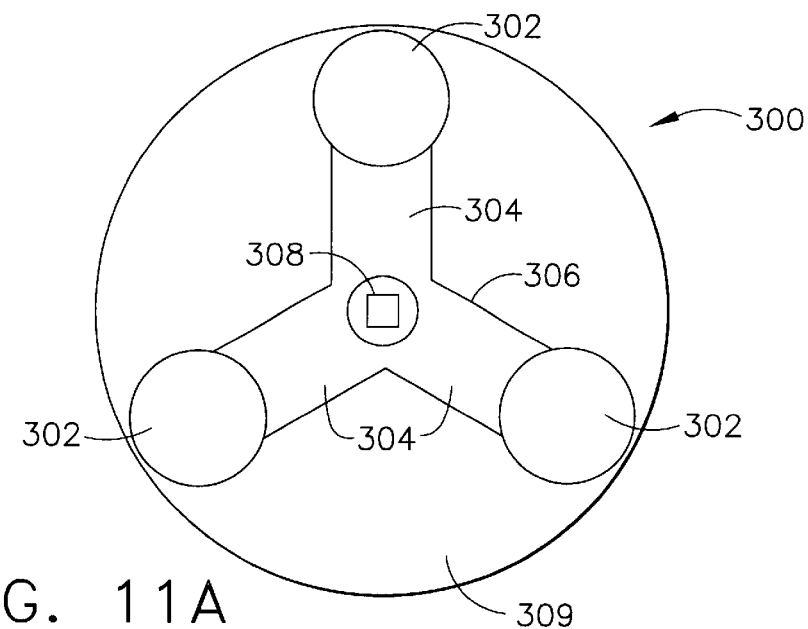
FIG. 11A is a schematic front view of yet another preferred embodiment of the present invention.
Figure 11B:
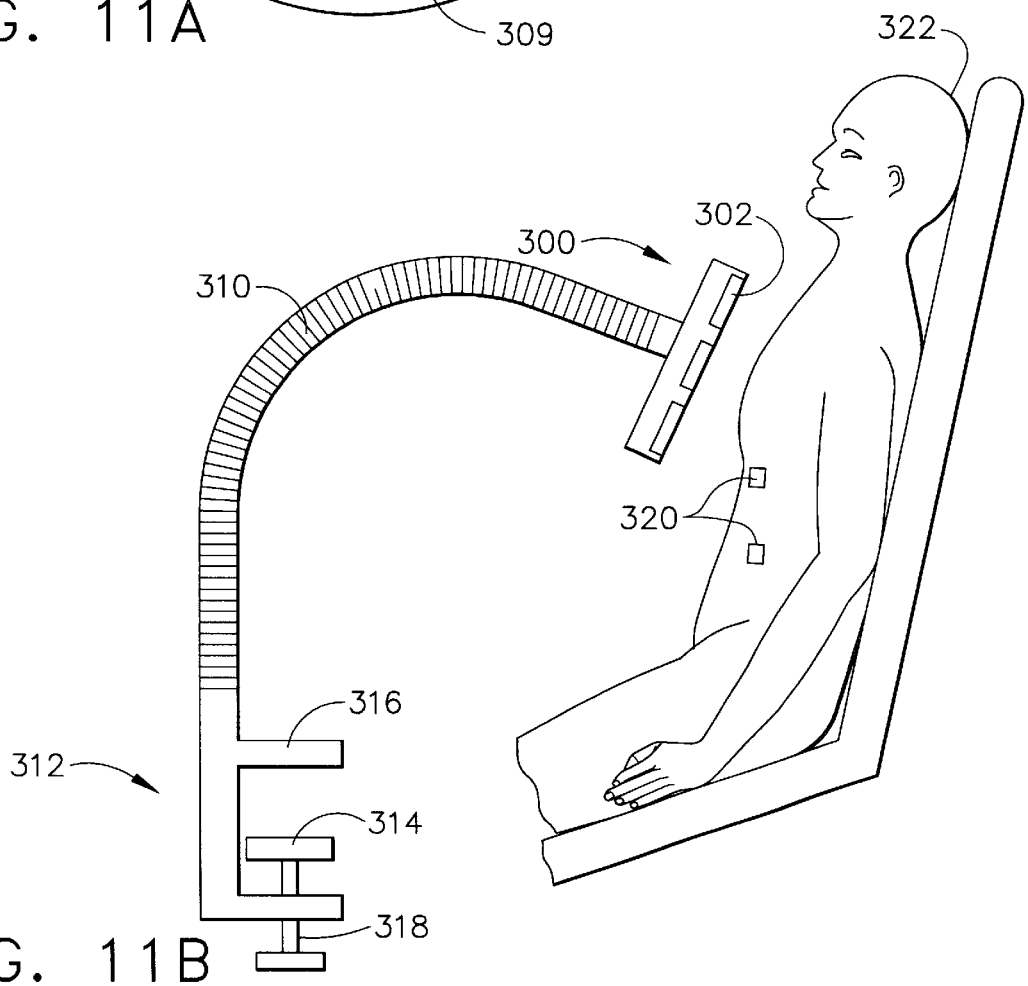
FIG. 11B is a side view of the preferred embodiment shown in FIG. 11A.

In another preferred embodiment of the present invention, such as shown in FIGS. 11A and 11B, a movable transducer assembly 300, also referred to as a "goose-neck" miniradiator, is shown, which includes one or more reference field transducers 302 which are preferably field transmitting coils of a very small size, and may incorporate ferrite cores. Small coils are preferred since they tend to act more like point source dipoles which provides more accurate calculations by the computer of probe disposition. Each coil 302 is attached to a coil retaining arm 304 forming support 306, which is preferably formed of a lightweight material such as plastic. At the center of support 306 is attachment bolt 308 which allows the support to be attached to a flexible, gooseneck arm 310 as shown in FIG. 11B. The entire movable transducer assembly 300 may be mounted to an operating table or the like by an adjustable mounting mechanism 312, which includes a movable bracket 314 tightenable against upper arm 316 by rotation of tightening screw 318. A support disk 309 is optionally included to provide enhanced support to the coils 302. Support disk 309, however, can be eliminated in situations where undesirable shadows may be cast due to lighting in the room in which the patient is located. Although three transducers 302 are preferred, one, two or more than three transducers can be used. For example, a single multi-axis, solid-state position sensor can be used where the probe transducers comprises field generating transducers.

As shown in FIG. 11B, one or more patient reference transducers 320 are attached to the body of patient 322 and used to determine the position of the transducers on the movable transducer assembly 300 with respect to the patient frame of reference after the movable transducer assembly is moved to its desired position. Preferably, patient reference transducer 320 comprises a solid-state 3-axis position sensor. Once the movable transducer assembly is moved into position, the disposition of the transducers on the movable transducer assembly with respect to the patient reference frame (as defined by the one or more patient reference transducers 320) can be determined in the conventional manner by transmitting and receiving non-ionizing fields between the patient reference transducers and the reference field transducers on the movable transducer assembly.

The movable transducer assembly 300 shown in FIGS. 11A and 11B is only one example of the support that can be used to provide readily repositionable reference field transducers. Other means for providing a movable and repositionable support can be employed, such as replacing goose neck arm 310 with a number of smaller rigid arm members attached to one another by adjustable and tightenable joints such as the joint and thumbscrew arrangement shown in FIG. 5. In addition, more than three coils can be employed on the movable transducer assembly and the coils need not be set in a co-planar relationship, so long as the relative positions among the coils is known or determinable.

Numerous advantages follow from the use of this movable transducer assembly. Importantly, the movable transducer assembly is movable close to the region of interest during the surgical procedure and also repositionable away from areas to which the surgeon must gain access. The movable transducer assembly is small and directable thereby providing an adjustable and stable suspension system for the field transducers for directing the fields created to the only the particular volume of tissue to be image correlated.

Superior signal-to-noise ratio performance is also achieved with the movable transducer assembly of the present invention. In general, with the use one or more transducers in a probe locating system, there is a region of volume associated with the transducers in which the signal-to-noise ratio of the assembly is optimized (a so-called "optimal region"), allowing higher accuracy field measurements to be made. With prior probe location systems in which the reference transducers are mounted in fixed positions about the patient bed, however, this optimal region will typically encompass a large area to account for possible movement of the probe throughout the patient. For example, if the probe such as a catheter must be tracked from the leg of the patient to the heart, the optimal region defined by the fixed transducers must be large enough to cover most of the patient. The larger the optimal regions, however, the more difficult it is to achieve a high signal-to-noise ratio throughout such region. With the movable transducer assembly of the present invention, this optimal area can be made smaller and highly concentrated since the assembly is movable, even during the surgical procedure, to the region of interest of the patient. Accordingly, preferred embodiments of the present invention can provide enhanced signal-to-noise performance in comparison to a fixed transducer assembly using the same transducers in a large fixed array. The signal-to-noise performance of the system also depends on the properties of the probe transducer. The enhanced performance provided by preferred embodiments of the present invention can provide acceptable signal-to-noise performance with a less sensitive probe transducer, which in turn facilitates miniaturization of the probe transducer and probe. Alternatively, the benefit provided by the movable transducer assembly can permit use of smaller, cheaper and less obtrusive reference transducers while maintaining satisfactory performance.

The movable transducer assembly can be optimally positioned so as not to obstruct the view of the assistant surgeon nor obstruct access to the patient. The movable transducer assembly may be attached to the operating bed rail and may be slid up and down the rail as desired. Since a patient reference transducer may be provided to account for the movement of the reference field transducers with respect to the patient, re-registration with the pre-acquired image data is readily accomplished.

Further, system software can also be provided and feedback techniques can be used to correct inappropriate placement of the movable transducer assembly. For instance, an indicator signal such as a light or tone can be generated when the positioning of the reference field transducers is too remote from the position sensor on the distal tip of the probe to generate reliable field detection and position information.

The use of small point source electromagnets is advantageous since they are lightweight and can therefore be readily and easily moved into desired positions, or out of the way of the physician, during a surgical procedure. The use of small point source electromagnets also allows more accurate computer modeling since the coils behave as better dipoles as compared to presently used fixed coil systems.

Moreover, with the coil arrangements such as the movable transducer assembly in accordance with the present invention, it is possible to reduce the separation between the plane of the radiators and the mapping volume to as small as inches and even fractions of an inch.

The coils arrangements of the present invention solve a number of problems caused by the use of fixed, non-movable coil systems. For instance, in spinal procedures, non-movable coil systems can obstruct the physicians and can block the assistant surgeon from standing opposite from the primary surgeon. Non-movable coil systems cannot generally be positioned above the patient as they would block the lighting. In addition, non-movable coil systems may not be positionable under the patient since the metal patient bed can cause interference and not all beds can be replaced or retrofitted to eliminate this problem. Thus current systems typically are provided parallel to the patient bed and can cause both visual and logistical obstructions. Moreover, with non-movable coils, high accuracy mapping volumes are too small to be useful if the coils cannot be moved from moment to moment.

Again, with the various embodiments of the present invention as described herein, a number of advantages are achieved, such as allowing the transducers to be moved closer to area of interest to provide better readings and allowing the use of even smaller transducers since the transducers can now be provided in a smaller, more focused area. The transducers can also be moved out of the way or to a new location for a particular procedure.

The present invention may also simultaneously use two or more sets of reference field transducers located at different areas on the patient, effectively defining two or more external reference frames. With this arrangement, the system can then be operative to switch between the sets of transducers as the probe moves between the transducer sets.

The present invention can also be used in conjunction with the system disclosed in U.S. application Ser. No. 08/476,380, the disclosure of which is hereby incorporated by reference. In the '380 application, adaptive feedback is used to adjust the currents supplied to the reference field transducers or coils to ensure that the sensor on the probe receive fields within a preselected range of magnitudes regardless of the location of the probe. This ensures that the sensor operates within its optimal range and allows the use of compact transmitters and sensors. Thus, the adaptive feed back techniques disclosed in the '380 application can be used with the present invention to adjust the strengths of the non-ionizing fields generated between the reference field transducers and the probe field transducer.

The present invention may further be used in conjunction with the "site probe/instrument probe system" disclosed in the PCT application field on even date herewith entitled "Medical Procedures And Apparatus Using Intrabody Probes" and which is commonly assigned to the assignee of the present application. In this site probe/instrument probe system, a medical probe such as a catheter is guided within the body of a patient by determining the relative positions of the probe relative to another probe, as by transmitting non-ionizing radiation to or from field transducers mounted on both probes. In particular, a site probe may be secured to a lesion within the body, and an instrument probe for treating the lesion may be guided to the lesion by monitoring relative positions of the probes. Simultaneous imaging of the disposition of the medical and/or imaging probe within the patient need not be provided since it may be only necessary to guide the instrument probe to the site prove to deliver medication or biopsy a tissue sample. The various movable transducer arrangements of the present invention can therefore be used with the site probe/instrument probe system, with or without simultaneous patient imaging, to locate the dispositions of the probes in the frame of reference defined by the reference field transducers.

As these and other variations and combinations of the features described above can be utilized without departing from the present invention, the foregoing description of the preferred embodiments should be taken by way of illustration rather than by way of limitation of the invention as defined by the claims.

INDUSTRIAL APPLICABILITY

The invention can be used in medical and related procedures.

What is claimed is:

1. A system for determining the disposition of a probe within the body of a patient, comprising:
    (a) a probe having one ore more probe field transducers mounted therein;
    (b) one or more reference field transducers mounted on a frame;
    (c) means for mounting said frame for movement relative to the patient so that said reference field transducers can be selectively positioned in different positions in close proximity to the body of the patient;
    (d) transmission means to transmit one or more non-ionizing fields between said probe field transducers and said reference field transducers;
    (e) detection means to detect each such transmitted field;
    (f) calculation means to determine the relative disposition of said probe with respect to said reference field transducers from properties of the detected fields and from the relative dispositions of said reference field transducers with respect to one another; and
    (g) translation means to translate the disposition of said probe relative to said reference field transducers to a known disposition relative to the body of the patient, said translation means including one or more fiducial transducers attachable to the body of the patient, said disposition of said one or more reference field transducers being determined by transmitting and receiving non-ionizing fields between the one or more fiducial transducers and the one or more reference field transducers.

2. A system as claimed in claim 1, wherein said one or more reference field transducers are in a known spatial relationship with respect to one another.

3. A system as claimed in claim 1, wherein said frame is rigid and holds said reference field transducers in fixed position relative to one another.

4. A system as claimed in claim 1, wherein said means for mounting comprises a flexible arm.

5. A method for determining the disposition of a probe within the body of a patient, comprising:
  (a) providing a probe having one or more probe field transducers mounted therein;
  (b) providing one or more reference field transducers mounted on a frame having means for mounting said frame for movement relative to the patient so that said reference field transducers can be selectively positioned in different positions in close proximity to the body of the patient;
  (c) adjusting said frame so that said reference field transducers are positioned in a first location in close proximity to the body of the patient;
  (d) transmitting one or more non-ionizing fields between probe field transducers and said reference field transducers;
  (e) detecting each such transmitted field;
  (f) calculating the relative disposition of said probe with respect to said reference field transducers from properties of the detected fields and from the relative dispositions of said reference field transducers with respect to one another; and
  (g) translating the disposition of said probe relative to said reference field transducers to a known disposition relative to the body of the patient, said translating step including the step of detecting non-ionizing fields transmitted between said reference field transducers and one or more fiducial transducers attached to the body of the patient.

6. A method as claimed in claim 5 further comprising the step of repositioning said one or more reference field transducers and then repeating the aforesaid steps.

7. A system for determining the disposition of a probe within the body of a patient, comprising:
  (a) a probe having one or more probe field transducers mounted therein;
  (b) one or more reference field transducers mounted on a frame;
  (c) means for mounting said frame for movement relative to the patient so that said reference field transducers can be selectively positioned in different positions in close proximity to the body of the patient;
  (d) transmission means to transmit one or more non-ionizing fields between said probe field transducers and said reference field transducers;
  (e) detection means to detect each such transmitted field;
  (f) calculation means to determine the relative disposition of said probe with respect to said reference field transducers from properties of the detected fields and from the relative dispositions of said reference field transducers with respect to one another; and
  (g) translation means to translate the disposition of said probe relative to said reference field transducers to a known disposition relative to the body of the patient, said translation means including means for determining the disposition of said reference field transducers relative to the patient including one or more patient reference transducers attachable to the body of the patient and computing the disposition of the probe relative to the patient based on the disposition of the reference field transducers relative to the patient, wherein the disposition of the reference field transducers is determined by transmitting and receiving non-ionizing fields between the one or more patient reference transducers and the reference field transducers.

8. A method for determining the disposition of a probe within the body of a patient, comprising:
  (a) providing a probe having one or more probe field transducers mounted therein;
  (b) providing one or more reference field transducers mounted on a frame so that said reference field transducers can be selectively positioned in different positions in close proximity to the body of the patient;
  (c) attaching one or more patient reference field transducers to the body of the patient;
  (d) adjusting said frame so that said reference field transducers are positioned in a first location in close proximity to the body of the patient;
  (e) transmitting one or more non-ionizing fields between probe field transducers and said reference field transducers;
  (f) detecting each such transmitted field;
  (g) calculating the relative disposition of said probe with respect to said reference field transducers from properties of the detected fields and from the relative dispositions of said reference field transducers with respect to one another; and
  (h) translating the disposition of said probe relative to said reference field transducers to a known disposition relative to the body of the patient, said translating step including the steps of determining the disposition of said reference field transducers relative to the patient by transmitting and receiving non-ionizing fields between the reference field transducers and the patient reference field transducers and computing the disposition of the probe relative to the patient based on the disposition of the reference field transducers relative to the patient.

9. A method as claimed in claim 8 further comprising the step of repositioning said one or more reference field transducers and then repeating the aforesaid steps.

* * * * *